United States Patent
Fischer et al.

(10) Patent No.: US 7,331,712 B2
(45) Date of Patent: Feb. 19, 2008

(54) X-RAY EXAMINATION APPARATUS THAT IS CONVERTIBLE AMONG MULTIPLE EXAMINATION CONFIGURATIONS

(75) Inventors: Klaus Fischer, Erlangen (DE); Wolfgang Zerl, Herzogenaurach (DE)

(73) Assignee: Siemens Aktiengesellschaft, Munich (DE)

(*) Notice: Subject to any disclaimer, the term of this patent is extended or adjusted under 35 U.S.C. 154(b) by 117 days.

(21) Appl. No.: 10/892,616

(22) Filed: Jul. 16, 2004

(65) Prior Publication Data

US 2005/0058257 A1  Mar. 17, 2005

(30) Foreign Application Priority Data

Jul. 17, 2003  (DE)  ............... 103 32 743

(51) Int. Cl.
  *H01J 35/16*  (2006.01)
(52) U.S. Cl. ............... 378/203; 250/519.1
(58) Field of Classification Search .......... 378/167, 378/172, 173, 177, 181, 182, 205, 206, 208, 378/209, 193–198, 203; 250/505.1, 519.1
See application file for complete search history.

(56) References Cited

U.S. PATENT DOCUMENTS

| RE20,641 | E | * | 1/1938 | Talty ............... 378/190 |
|---|---|---|---|---|
| 3,149,229 | A | * | 9/1964 | Morel ............... 5/601 |
| 3,984,696 | A | * | 10/1976 | Collica et al. ........ 250/519.1 |
| 4,062,518 | A | * | 12/1977 | Stivender et al. ...... 250/519.1 |
| 4,365,344 | A | * | 12/1982 | Dornheim ............ 378/189 |
| 4,379,348 | A | * | 4/1983 | Haas et al. .......... 378/57 |
| 4,581,538 | A | * | 4/1986 | Lenhart ............. 250/519.1 |
| 5,023,899 | A | * | 6/1991 | Ohlson ............... 378/196 |
| 5,561,699 | A | * | 10/1996 | Fenner .............. 378/208 |
| 5,768,336 | A | * | 6/1998 | Khutoryansky et al. .. 378/116 |
| 5,900,638 | A | * | 5/1999 | Jaeger et al. ........ 250/519.1 |
| RE37,614 | E | * | 4/2002 | Ohlson ............... 378/177 |
| 6,471,167 | B1 | * | 10/2002 | Myers et al. ......... 248/177.1 |
| 6,944,897 | B2 | * | 9/2005 | Koch ................. 5/621 |

FOREIGN PATENT DOCUMENTS

| DE | G 88 07 462.5 | 11/1989 |
|---|---|---|
| DE | 297 06 321 | 7/1997 |
| EP | 0 303 214 | 4/1989 |
| EP | 393214 A1 * | 10/1990 |
| WO | WO 02/15198 | 2/2002 |

OTHER PUBLICATIONS

Jacobson, "Radiation Protection Considerations of Overhead Fluoroscopic Installations", Jan. 1971, Health Physics, vol. 20, pp. 55-58.*

(Continued)

*Primary Examiner*—Edward J. Glick
*Assistant Examiner*—John M Corbett
(74) *Attorney, Agent, or Firm*—Schiff Hardin LLP

(57) ABSTRACT

An X-ray system has a patient examination table, an image acquisition unit under the surface of the patient examination table, and an X-ray radiator that can be positioned above the patient examination table, On the patient examination table a radiation protection device is disposed, which—during the operation—shields at least one zone on one side of the patient examination table from the radiation area between the X-ray radiator and the image acquisition unit. In addition, on the patient examination table an X-ray system operation unit is disposed that is accessible from the shielded zone.

22 Claims, 9 Drawing Sheets

OTHER PUBLICATIONS

Brateman, "The AAPM/RSNA Physics Tutorial for Residents—Radiation Safety Considerations for Diagnostic Radiological Personnel", 1999, Radiographics: Imaging and Therapeutic Technology, vol. 19, No. 4, pp. 1037-1055.*

* cited by examiner

X-RAY EXAMINATION APPARATUS THAT IS CONVERTIBLE AMONG MULTIPLE EXAMINATION CONFIGURATIONS

BACKGROUND OF THE INVENTION

1. Field of the Invention

The invention relates to an X-ray system of the type having a patient examination table, an image acquisition unit underneath the surface of the patient examination table (such as a flat detector), and an X-ray generator mounted above the table.

2. Description of the Prior Art

An X-ray system of this described type is a typical so-called "overtable system". Such an overtable system usually is controlled by means of a main control console located outside the X-ray examination room. The operator can watch the patient through a glass wall between the control room and the X-ray examination room, and interacts with the patient via a voice communication system. In addition to overtable systems, so-called "undertable systems" also are known, in which the X-ray generator is located underneath the table and the image acquisition unit, usually an image intensifier or a fluorescent screen, is mounted above the patient examination table. In the undertable system, the operator is directly present with the patient and, therefore, can touch and/or turn the patient during the imaging or X-ray. During the procedure, the operator is protected from X-ray radiation by lead-lined rubber gloves and a lead-lined apron or a lead coat, as well as by appropriate shielding equipment mounted on the patient examination table. In both versions, the image data can be transmitted from the image acquisition unit to an image-viewing screen installed beside the table or at the control console. During the examination, the operator can view the images immediately. Undertable and overtable systems each have their own advantages and disadvantages. The substantial advantage of an undertable system is the availability of direct contact with the patient during the examination. The advantage of the overtable system consists in the fact that the operator has better radiation protection. Another basic advantage of the overtable system is its superior image geometry, because the distance of the detector-focus in relation to the object-focus distance is better than in the undertable system. This automatically results in a better image quality. Whether an undertable or an overtable system is used for a certain examination depends on the type of examination as well as on the "examination philosophy" of the particular physician, which is usually determined by his/her education history.

A system disclosed in PCT Application WO 02/15198 has a C-arm, with the X-ray generator being located underneath the patient examination table.

U.S. Pat. No. 5,900,638 also describes an X-ray diagnostic device located above the patient examination table so that the X-ray generator must be located underneath the table.

In order for physicians in a consulting room or a clinic to have the option of obtaining images using either the undertable procedure and the overtable procedure, at the present time both an undertable and an overtable systems must be available, and usually are installed in different rooms. It is clear that an installation with several imaging devices—especially if these instruments are up-to-date, including expensive dynamic flat detectors—is very costly. Although, generally the various devices can be used in parallel practice shows that, in a joint consulting room, for example, several physicians use the overtable system for their examinations, whereas the undertable system is not sufficiently utilized (or vice versa). Thus, a rational utilization of the systems with a simultaneous reduction of the waiting times requires costly planning and scheduling of examinations. In some cases—especially in emergency cases—this planning must be overridden. Thus, the result is that, at least temporarily, these instruments are not optimally used and, on the contrary, the staff and the patients face unnecessary waiting times.

SUMMARY OF THE INVENTION

An object of the present invention is to provide an alternative to the described state of the art.

This object is achieved by an X-ray system according to the invention having a radiation protection device disposed on the patient examination table. The radiation protection device protects at least a zone on one side of the patient examination table from the radiation between the X-ray radiator and the image acquisition unit. In addition, the system has an X-ray system operation unit, which is accessible from the shielded zone.

Using this radiation protection device and the operation unit installed directly on the patient examination table, the operator is provided with a system control that is close to the patient, and also with protection from radiation analogous to that of an undertable system; i.e., the technician can operate the system exactly like an undertable system with the added advantage of the better image geometry of an overtable system.

The X-ray system preferably also has a remote control unit with which to operate the system components from an adjoining room. With this configuration, the system can be alternatively operated as a conventional undertable system or as an overtable system. Therefore, the installation of two independent X-ray systems in different rooms is no longer necessary. The system is better utilized and always provides an optimal image geometry.

In general, the operation unit can be arranged at any place on the patient examination table, for example, in a housing installed directly on the front side of the patient examination table. In a preferred embodiment the operation unit is mounted directly on the radiation protection device or integrated in the radiation protection device. This design ensures that, in a normal situation, i.e., when standing in a normal position in front of the operation unit, the operator is automatically within the shielded zone.

The radiation protection device and the operation unit preferably are mounted on the patient examination table so that they can be shifted in the longitudinal direction of the patient examination table. With this adaptability, the operator can optimally set the position of the radiation protection device and his/her own position with respect to the region in the patient's body to be examined.

In a preferred embodiment of the invention, the radiation protection device has a bridge-shaped radiation protection housing, which, during the operation, extends transversally across the patient examination table between the X-ray radiation and the image acquisition unit, and has a tunnel-like aperture for the person to be examined, who is positioned on the patient examination table.

Each of the bridge-shaped radiation protection housing and the operation unit preferably is mounted on the patient examination table in such a manner that they can be swiveled to and from the surface of the patient examination table. Alternatively, or in addition, the radiation protection housing and/or the operation unit is/are connected to the patient examination table in a detachable manner—preferably in the form of a quick-lock closure system. With the radiation protection housing swiveled away or completely removed from the radiation protection housing, the system—not hindered by the radiation protection housing—can be used as a fully functional regular overtable system.

In a preferred embodiment of the invention, the radiation protection housing has a first sidewall that is mounted on one longitudinal side of the patient examination table and that, with the radiation protection housing in an operational position, extends upwardly, and also Includes a spanning wall disposed at the top of the sidewall. The spanning wall extends across the patient examination table toward the other longitudinal side of the patient examination table and has at least one zone that is penetrable by X-rays. This X-ray-penetrable zone can be an aperture or a zone in the ceiling wall made of X-ray-penetrable material. In close-to-the-patient operation, the X-ray radiator is placed directly on or relatively close to the spanning wall in such a manner that, through the X-ray-penetrable zone, the X-rays reach the patient and then the image acquisition unit located underneath the patient, i.e., underneath the table.

The first sidewall preferably is located on the opposite side of the operation unit, i e., on the "reverse side" of the patient examination table. If the radiation protection housing and the operation unit are connected to the patient examination table in a detachable manner, there exists the possibility of attaching these components on either longitudinal side of the patient examination table so that, depending on the type of examination, the operator can stand to the right or left of the patient.

In addition, the radiation protection housing preferably has, on one of the two sides adjacent to the first sidewall, or on the side opposite to the first side (i.e., on the "front side" of the patient examination table), shielding shade elements that hang from the spanning wall and form a flexible sidewall. With this configuration, the operator has the option, while using appropriate protective lead-lined rubber gloves, of reaching through the wall formed by the shielding shade elements and touching the patient in the examination zone during the examination.

The image acquisition unit preferably is a flat detector, which requires relatively little space. The image acquisition unit preferably is mounted in the patient examination table such that it can be moved, preferably by a motor, In a direction along the table and/or in a direction transverse to the table.

The image acquisition unit preferably is mounted at the patient examination table such that it can be swiveled into or out of the table plane. In a preferred design, the image acquisition unit can be transferred to a side position above the patient examination table. This can be achieved either by reversing or swiveling and/or shifting the image acquisition unit from a position underneath the patient examination table into a side position.

The X-ray radiator preferably hangs from a generator stand, which is designed in such a manner that the X-ray radiator is adjustable in at least three (orthogonal) spatial directions, and can be swiveled around its vertical and horizontal axes. The combination of any desired swiveling and adjustment possibilities of the image acquisition unit and the extensively variable positioning of the X-ray radiator make it possible to irradiate the patient from various directions, which is currently only possible when using a C-arm unit, Furthermore, the stand preferably is designed so that the X-ray radiator also can be moved to a position outside the area above the patient examination table. If the X-ray generator can be moved beside the patient examination table, using a mobile detector or a conventional film cassette, X-ray images can be made even of a patient lying in a hospital bed without having to transfer the patient to an examination table. The stand preferably is designed so that the X-ray generator also can be positioned directly in the side of the patient examination table and swiveled around the horizontal axis a sufficient amount so that transverse images of a patient lying on the table can be obtained after, as already described, the image acquisition unit has been brought to a position to the side of and above the patient examination table.

The examination table itself preferably is designed so that the table base, on which a table plate is arranged, is located completely underneath the table plate so that the table is accessible from all sides.

The table base preferably is designed and connected with the table plate so that the table plate can be tilted around an axis perpendicular to the longitudinal direction of the table. The angular range within which the table plate can be tilted preferably is large enough so that the table plate can be tilted into a vertical position, and the table together with the image acquisition unit mounted on it can be used as a wall stand. The table base can be attached to the table plate so that it can be moved, without the need for any intermediate stages, from about −30° (in the direction of the head side of the table plate) to +90° (in the direction of the foot side of the table plate), i.e., into the desired vertical position.

The position of the X-ray radiator, the position of the image acquisition unit on the patient examination table, and the position of the table plate all preferably can be set by means of a motor. For this purpose, the X-ray system is equipped with a control unit for the automatic positioning, i.e., moving and/or swiveling of the image acquisition unit and/or the X-ray radiator and/or the patient examination table, wherein the operation unit mounted on the patient examination table or a remote control console outside the X-ray room can be used.

The control unit should be used so that, during the positioning of the X-ray generator, the image acquisition unit is automatically moved so that the image acquisition unit is or remains centered on a central X-ray beam generated by the X-ray radiator. This means that the control unit electronically controls the image acquisition unit and the X-ray radiator, so that a centered position of the image acquisition unit in relation to the X-ray generator is always ensured, in a fashion similar to that of a C-arm device.

Furthermore, the control device preferably is designed so that, during positioning of the examination table, the X-ray radiator is automatically moved in such a manner that—in relation to the table—the set-up position and the set-up radiation angle of the central X-ray beam remain constant. Thus, using this control device, the X-ray system can be used as a C-arm device and, therefore, can fully substitute for it. Since the coupling is done electronically and—unlike a C-arm device—no mechanical connection is required between the X-ray radiator located above the patient examination table and the image acquisition unit located underneath the patient examination table, complete access to the table from all sides is guaranteed.

For the control of the X-ray radiator and/or the image acquisition unit and/or the patient examination table, the control unit preferably can be deactivated so that the aforementioned components can also be positioned manually. In this case, the positioning data of the relevant component is determined for adjusting the remaining components, if necessary, but a free manual operation of the relevant component is also possible. Moreover, the electronic coupling of the individual components can be deactivated so that, at any time, the operator has the option of positioning all components manually or of automatically controlling each component independently, if the situation so requires.

DESCRIPTION OF THE PREFERRED EMBODIMENTS

Figure 1:
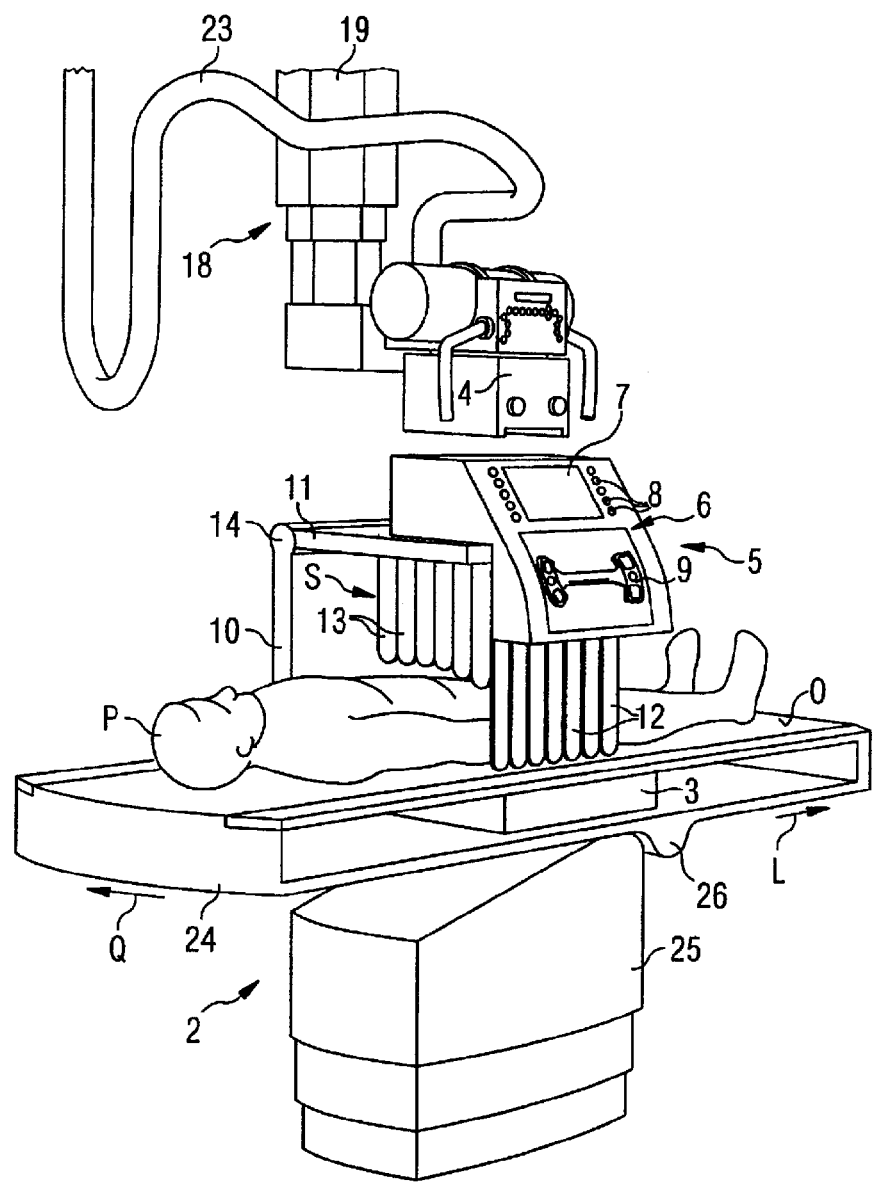
FIG. 1 is a perspective view of an exemplary embodiment of an X-ray system according to the invention in close-to-the-patient operation with a radiation protection housing above the patient examination table.

All the figures show the same universal X-ray system 1, which is can be substituted for a basic imaging device, an overtable device, an undertable device, and a C-arm device. For simplicity, not all the figures show all the components. So, for example, the power supply line 23, which leads from the top to the X-ray radiator 4, is shown only in FIGS. 1 and 2, and the control unit 27 for the positioning of individual components 2, 3, 4 is shown only in FIG. 7.

In addition to the illustrated components, the X-ray system 1 has one or more monitors on which the operator can view the image acquired by an image acquisition unit 3, here a flat detector 3. These monitors can be mounted, for example, on a second ceiling stand (not shown) beside the table 2. Also not shown are other components located outside the X-ray room, such as the main control console, additional monitors, etc., as well as other components required and usual for such a system, such as a voltage generator, imaging computer, data storage devices and/or interfaces to connect the system to a radiology information system or similar systems.

A basic component of the X-ray system 1 shown in the figures is a patient examination table 2 with a table base 25 and a table plate 24 mounted thereon. The table plate has a surface O, on which a patient P can be placed.

A flat detector 3 is installed in the table plate 24 in such a manner that it can be moved in the longitudinal direction L and in the transversal direction Q of the table plate 24.

An X-ray radiator 4 hangs on a ceiling stand 18 above the table 2. The design of the ceiling stand 18 can best be seen in FIG. 9. The ceiling stand 18 has a telescopic arm 19, which is mounted on a carriage 22. This carriage 22 hangs on rails 21, on which the carriage 22 can be moved in a first spatial direction (in direction y) parallel to the transversal direction Q of the patient examination table 2. This rail system hangs on a rail 20 that extends vertically to the direction y (in direction x). The entire stand 18 can be moved along the rail 20 parallel to the longitudinal direction L of the patient examination table 2.

The X-ray radiator 4 hangs, on the bottom thereof, on the telescopic arm 19 and thus can be moved up and down (direction z). In addition, the X-ray radiator 4 can be swiveled around a vertical rotation axis DV that extends coaxially to the telescopic arm 19, and around a rotation axis DH that extends, at the end of the telescopic arm 19, perpendicularly to the rotation axis DV. With this equipment in place, the X-ray radiator 4 can be oriented in any direction as shown in the FIGS. 4 to 8. This variability in the positioning of the X-ray radiator 4 allows one to irradiate the patient from any angle both in the longitudinal and the transverse directions.

Figure 9:
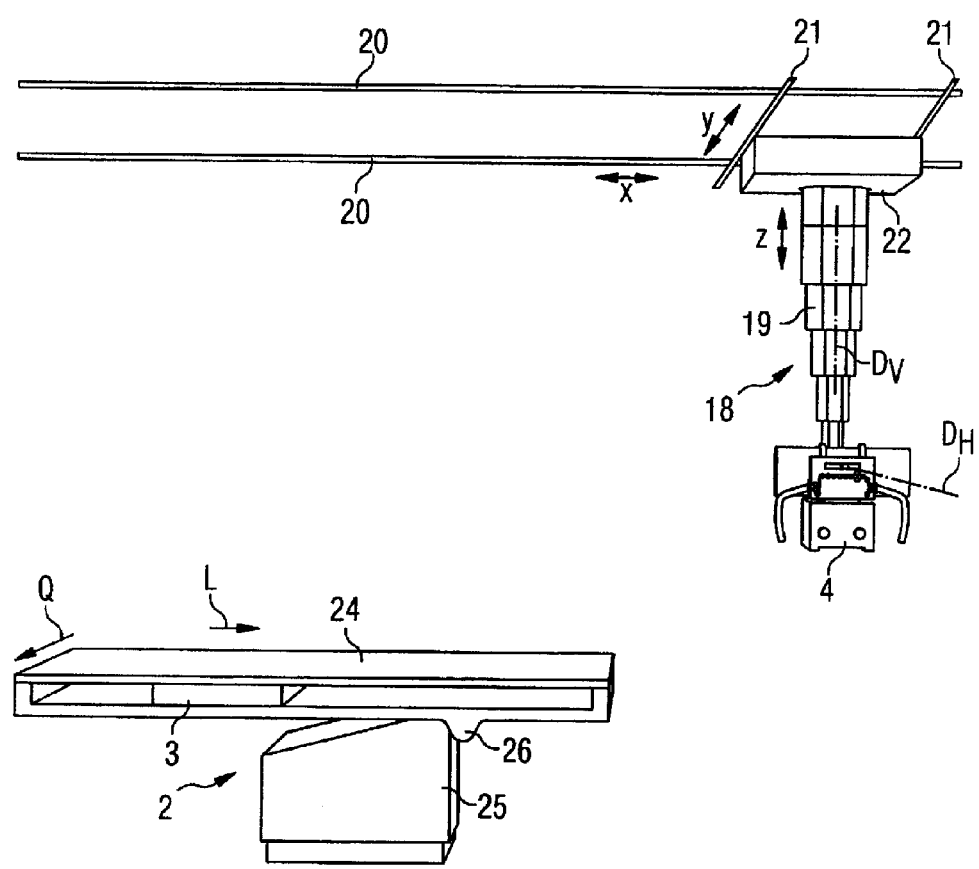
FIG. 9 shows the X-ray system according to FIGS. 1 to 8, with the X-ray generator moved outside the patient examination table.

The ceiling stand 18 with the X-ray radiator 4 can be moved in at least one spatial direction (here in direction x along the rail 20) in order to reach a position beside the patient examination table 2 (FIG. 9). With the X-ray radiator 4 in this position, it is possible to move a bed-ridden patient underneath this X-ray radiator 4 and make an X-ray image using a mobile detector or a conventional film cassette, all without having to transfer the patient from his/her bed onto the patient examination table 2.

Figure 5:
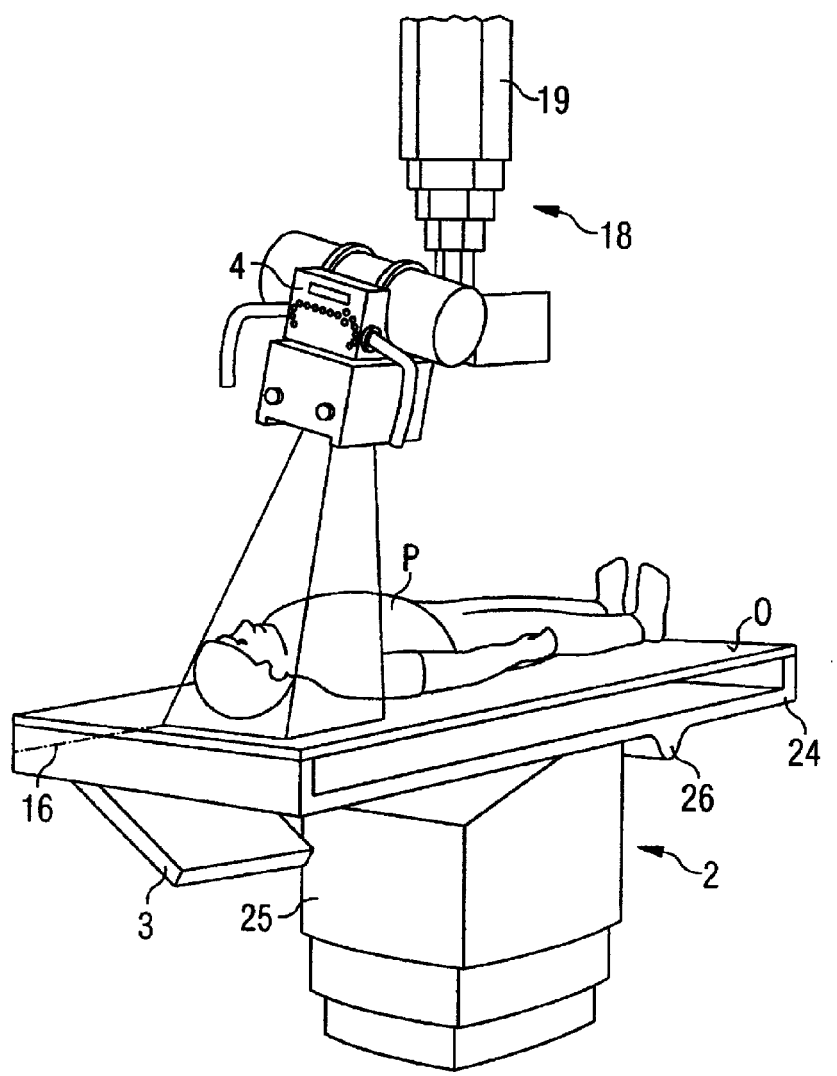
FIG. 5 is a perspective view of the X-ray system according to FIG. 3, with the X-ray generator and the detector inclined in relation to the transversal direction of the patient examination table.

The flat detector 3 arranged inside the table plate 24 can be freely moved, either by a motor or manually, both in the longitudinal direction L and the transversal direction Q of the patient examination table 2. In addition, there is the possibility of tucking the detector 3 away around a rotational axis 16, Thus, it is possible in combination with a corresponding tilted position of the X-ray radiator 4, to perform inclined radiation, as is currently only possible using a C-arm stand, i.e., an angular setting, in which the detector 3 and the central beam of the X-ray radiator 4 are always oriented vertically to each other (FIG. 5). The detector 3 is mounted on the table plate 24 in such a manner that it can optionally be tucked away either around the rotation axis 16 shown in the FIG. 5 or around a rotation axis (not shown) that extends parallel on the other longitudinal side of the table plate 24, i.e., in the opposite direction.

Figure 6:
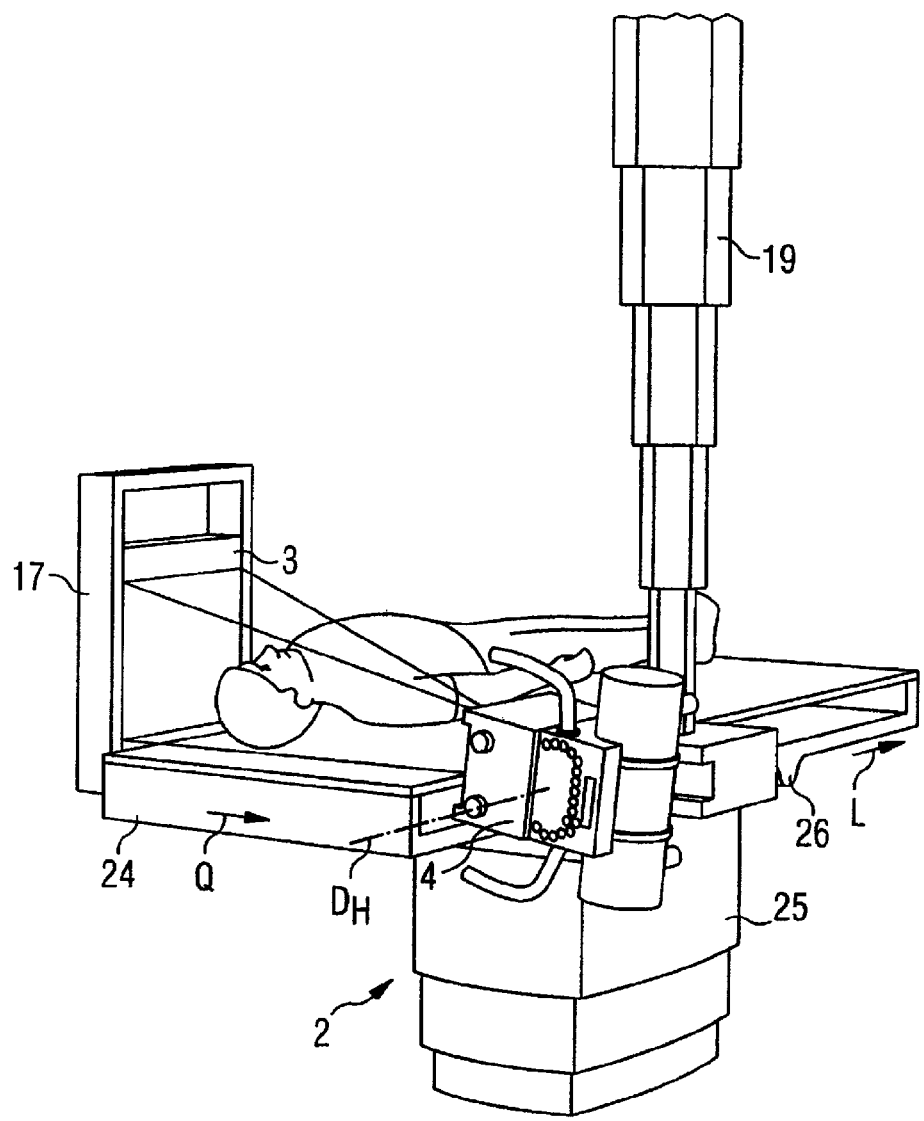
FIG. 6 is a perspective view of the X-ray system with the detector swiveled up sidewise, and the X-ray generator arranged on the side of the patient examination table to perform a side image of a patient.

Such an extension mechanism also allows one to place the flat detector 3 in a vertical position outside the table plate 24 (FIG. 6). For this purpose, the detector 3 is preferably mounted in a carrying frame 17 (as shown in FIG. 6) and, therefore, can be moved in this position in a vertical direction. The detectors 3 can be swiveled up to a vertical position on the left side of the patient (as shown in FIG. 6), and also to the patient's right.

As is also shown in FIG. 6, the telescopic arm 19 is designed in such a manner that the X-ray radiator 4 can be moved all the way to the surface O of the table. By turning the X-ray radiator 4 around the horizontal rotation axis $D_v$, the X-ray radiator 4 can be brought into the desired position so that a lateral image is then possible. This procedure requires that the stand 18 can be moved in the direction y, i.e., parallel to the transversal direction Q of the patient examination table and over the entire width of the table.

Figure 8:
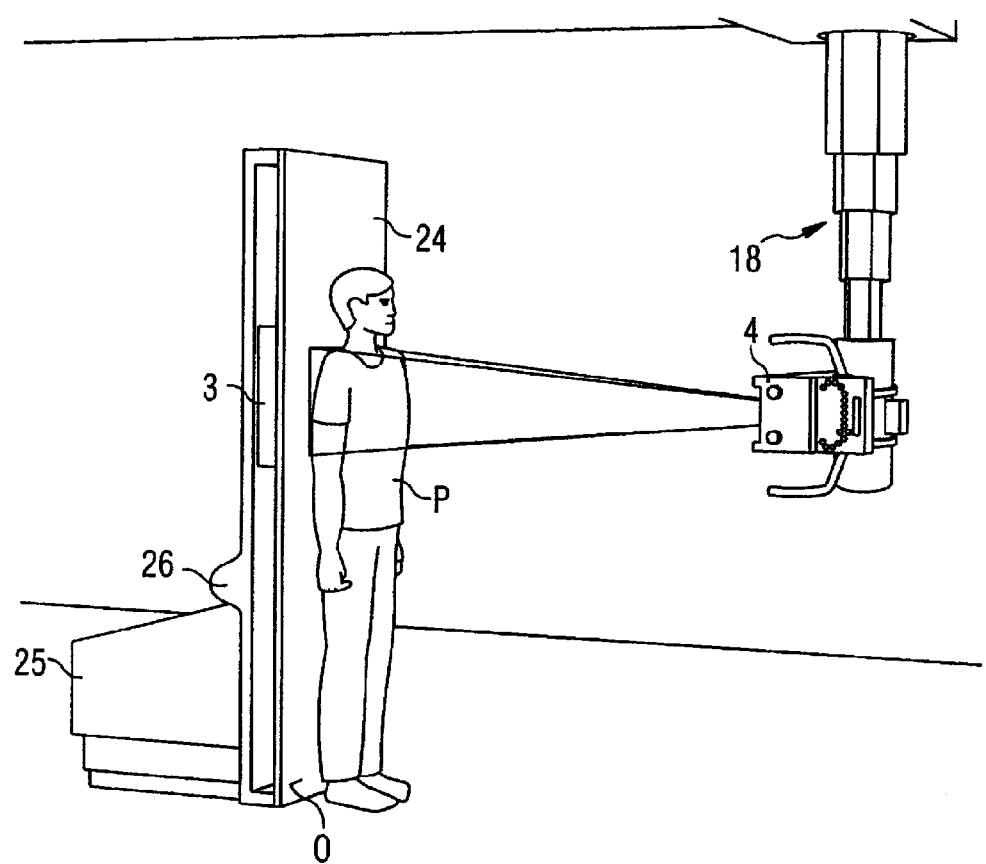
FIG. 8 shows the X-ray system according to FIGS. 1 to 7, with the table plate tilted in a vertical position to be used as a wall stand.

The patient examination table 2 preferably is designed in such a manner that the table base 25 is arranged completely under the table plate 24. The table base 25 preferably is designed in the form of a telescopic column so that the patient examination table 2 can be moved up and down over a wide range. The table plate 24 is connected with the table base around a rotation axis 26 that extends perpendicularly to the longitudinal direction L of the table 2 so that the table plate 24 can be tilted. The rotation axis 26 is located at one of the edges of the table base 25 so that the table plate 24 can be inclined towards the base up to 90°; i.e., it can take up a vertical position (FIG. 8). In this position, the table plate 24 serves as a wall stand in which the flat detector 3 is mounted so that it can be moved vertically. The patient then stands in front of the table plate 24.

Due to the beveled upper side of the table base 25 on the head side of the table plate 24, it is possible to tilt the table plate 24 (even in the head direction) by about 30°. The type of support provided to the table plate 24 by the table base 25 still ensures a very stable construction that allows it to handle even very heavy patients who weigh more than 440 pounds.

Figure 7:
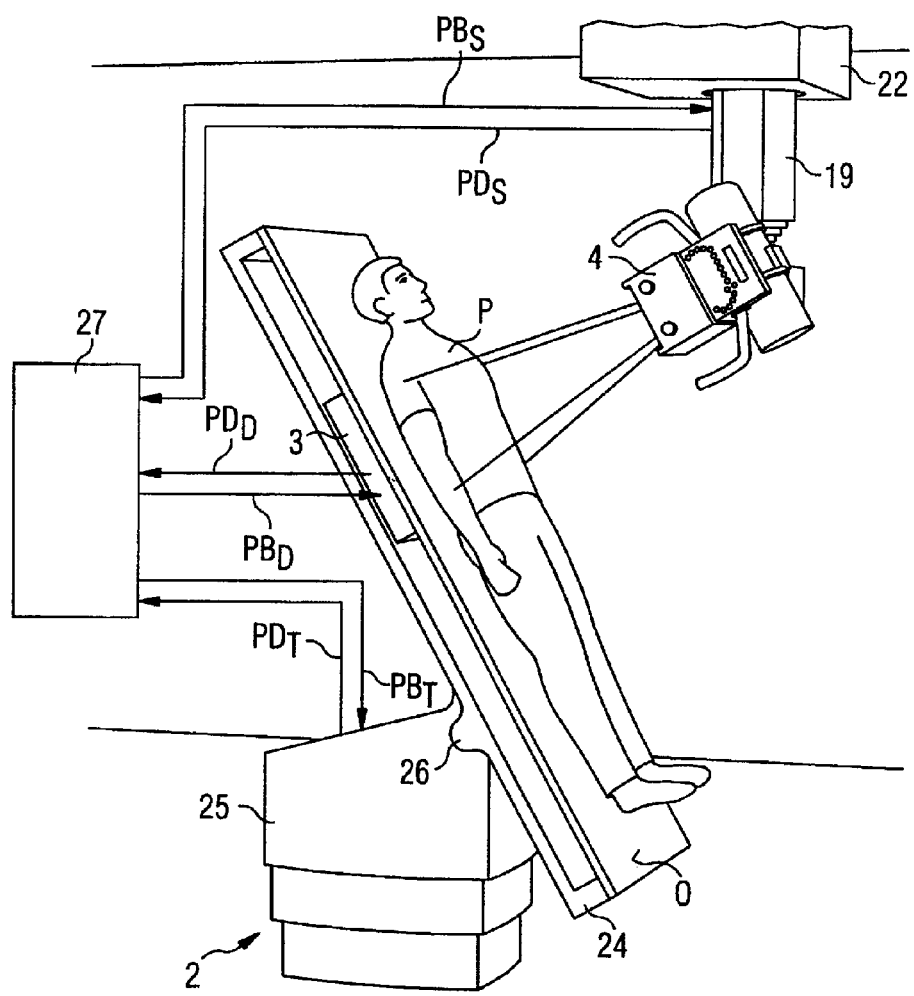
FIG. 7 is a perspective view of the X-ray system according to FIGS. 1 to 6, with the table plate tilted and with a schematic view of a control unit for the positioning of the X-ray generator, the image acquisition unit, and the patient examination table.

All movable components, such as the patient examination table 2, the flat detector 3, and the X-ray radiator 4 or the stand 18 of the X-ray radiator 4, can be positioned by a motor using the control device 27. For this purpose, the control device 27 sends positioning commands $PB_D$, $PB_T$, $PB_S$ to the individual components 2, 3, 4 and/or to the motors or other actuators located therein (as shown in FIG. 7). The control device 27 receives position data $PD_D$, $PD_T$, $PD_S$ from the actuators or by means of additional position-determining sensors (not shown). Using this data, the control device 27 can determine, at any time, the actual positions of the components 2, 3, 4.

The control device 27 is designed so that, for example, the X-ray radiator stand 18 is electronically coupled with the table 2 so as to ensure that the X-ray radiator 4 follows every tilting of the table or other movements in such a manner that the position and the radiation angle of the central beam remain unchanged in relation to the table and thus to the detector 3 and the patient P. Also, the flat detector 3 can be electronically connected to the X-ray radiator 4 in such a manner that the flat detector 3 moves synchronously with the movements of the X-ray radiator 4 (or vice versa) so that the initially set-up direction of the central beam remains constant in relation to the flat detector. Thus, no mechanical parts are required in order to connect the X-ray radiator 4 or the stand 18 and the table 2 or the flat detector 3, which is, by contrast, the case with a C-arm. With the design of the table, the operator has free access to the patient from any direction.

The electronic control of the individual components 2, 3, 4 can be deactivated. So it is possible, for example, to manually set up the X-ray radiator stand 18 as is also the case with an up-to-date three-dimensional stand. It is possible, in spite of the manual adjustment of the X-ray radiator 4, for example, to maintain the coupling between the X-ray radiator 4 and the detector 3, i.e., the position data PBS of the X-ray radiator 4 continues to be transmitted to, and evaluated by, the control device 27.

Thus, even with the manually set X-ray radiator 4, the flat detector 3 can automatically follow so that the detector 3 remains centered on the beam path.

In addition, the represented X-ray system 1 has, as a basic component essential, a radiation protection device 5 disposed on the patient examination table 2 and an X-ray system operation unit 6 also mounted on the patient examination table 2. In the represented preferred embodiment of the invention, the radiation protection device is a radiation protection housing 5, which—when in operation—extends like a bridge between the X-ray radiator 4 and the flat detector 3 across the patient examination table 2. A tunnel-like aperture for the patient (see FIG. 1) exits between the radiation protection housing 5 and the surface O of the patient examination table 2. In this case, the operation unit 6 is integrated in the radiation protection housing 5.

The radiation protection housing 5 has a first sidewall 10 that is mounted on one longitudinal side of the patient examination table 2 that extends upwardly (in FIG. 1 on the rear longitudinal side of the table plate 24), and a spanning wall 11 at the top of the sidewall 10 and extending across the table plate 24. This spanning wall 11 has, in its middle area, an aperture (not shown) for the X-radiation. When the radiation protection housing 5 is used, the X-ray radiator 4 is placed directly at or above this aperture.

On the side opposite the first sidewall 10, there hang lead shielding shade elements 12, which form a flexible front wall as radiation protection for the operator. Above this wall composed of shielding shade elements 12 at the front edge of the spanning wall 11 is located the operation unit 5, which in this is a touch display 7 beside which are control buttons 7 and underneath which is a handle 9.

In addition, further shade elements 13 are disposed on the side that is adjacent to the first sidewall 10 and which is oriented in the direction of the foot end of the table plate 24. These shade elements ensure shielding in the direction of the feet of the patient P. Furthermore, protective shade elements (not shown) also can hang on the head side of the radiation protection housing 6.

The operator standing beside the patient and in front of the operation unit 6 is well shielded by the radiation protection housing from the radiation area S between the X-ray radiator 4 and the detector 6, especially the lateral shades 12, 13.

During the examination, using appropriate protective gloves, the operator can shift the shielding shade elements 12 and 13 and touch the patient. Due to this design feature, the X-ray system provides the same functionality as a conventional undertable device, with the added advantage of the possible angular images enabled by the free adjustability of the X-ray radiator 4 and the mobility of the flat detector 3.

The radiation protection housing 5 can be moved in the longitudinal direction L of the table, wherein the flat detector 3 can be coupled, mechanically or electronically, with the housing 5 and thus synchronously moved. In this undertable operation, too, the X-ray radiator is coupled, preferably electronically, with the flat detector and is, for example, automatically moved whenever the radiation protection housing 5 is moved by its handle 9 and the flat detector 3 is simultaneously displaced. The operator can also move the components by means of a motor and the control device 27 using the operation unit 6 mounted on the patient examination table 2. Alternatively, the system can be operated from a main control console located in an adjacent room.

The radiation protection housing 5 with the operation unit 6 can be uncoupled from the patient examination table 2 and attached on the other side, i.e., on the front side to the right of the patient, as shown in FIG. 1.

Figure 2:
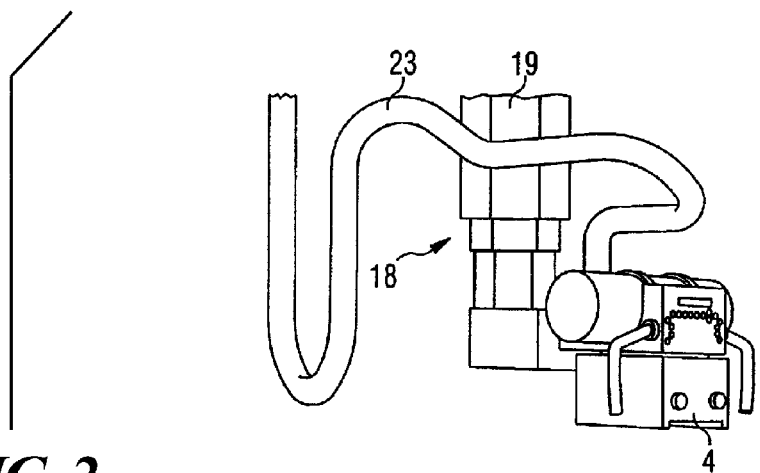
FIG. 2 is a perspective view of the X-ray system according to FIG. 1, with the radiation protection housing swiveled away.
Figure 2:
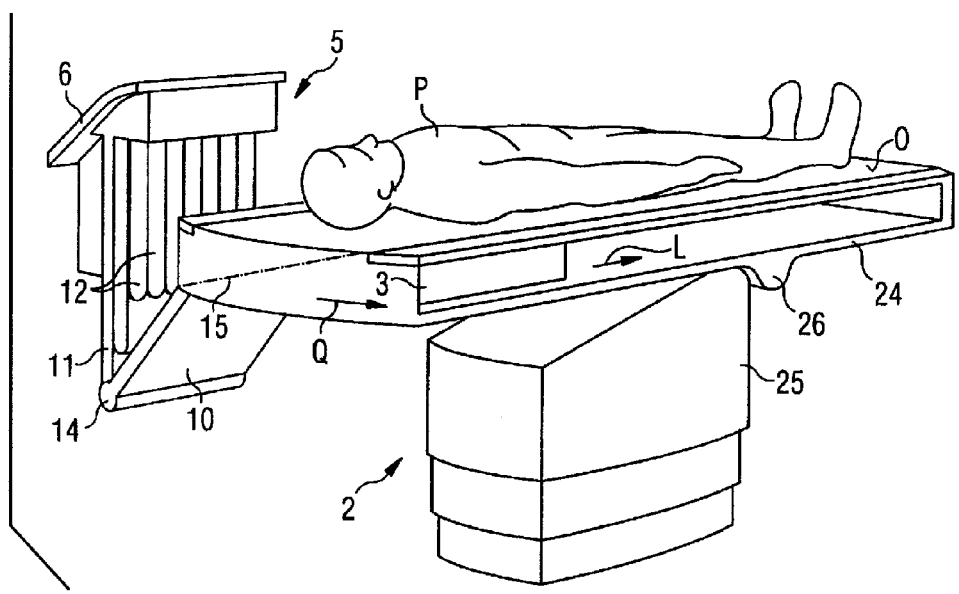
Figure 3:
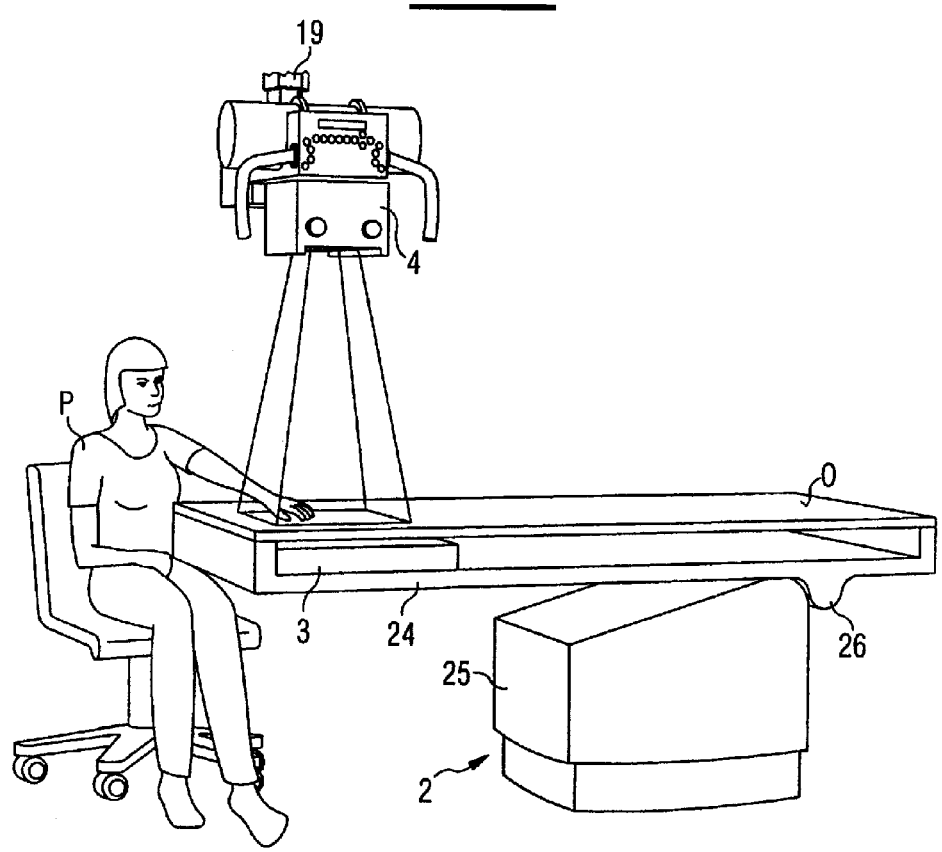
FIG. 3 is another perspective view of the X-ray system according to FIGS. 1 and 2, with the radiation protection housing reversed, and with a straight setting of the X-ray beam to be used as a basic imaging device.
Figure 4:
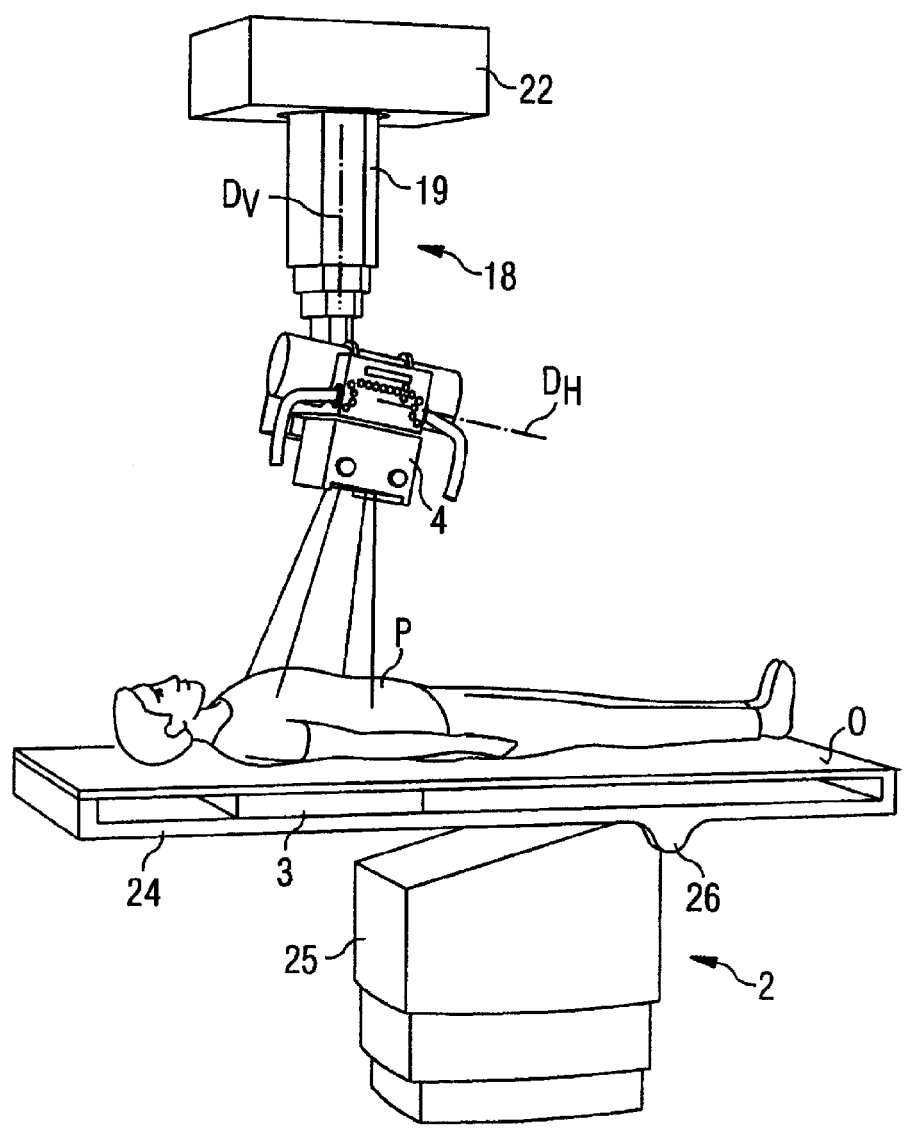
FIG. 4 is a perspective view of the X-ray system according to FIG. 3, with the X-ray generator inclined in relation to the longitudinal direction of the patient examination table.

In addition, the radiation protection housing 5 can be tucked away toward the side of the table 2, on which the rear wall of the housing is located as shown in FIG. 2. For this purpose, the first sidewall 10, i.e., the rear wall 10, can be flipped around a rotation axis 15 on the rear edge of the table surface 24, and is then fixed in at least the two end positions. Moreover, the ceiling wall 11 can be swiveled around a rotation axis 14 and can be fixed and connected to the sidewall 10 in its end positions. With the radiation protection housing 3 flipped over to the back, the shades 12 automatically rest on the ceiling wall 11, or can even be removed.

In this way, by means of a simple swiveling, the X-ray system can be switched from a close-to-the-patient "undertable operation mode" to a normal overtable operation mode.

Consequently, the X-ray system 1 combines, in a single device, the advantages of a fully functional overtable system with those of an undertable system. Direct access to the patient is possible during the examination. During a close-to-the-patient operation mode, the operator is sufficiently protected from radiation, while the whole procedure can be run from an area close to the patient. The system also allows for the manual positioning of its individual components in relation to the patient. Due to the smaller object—image acquisition unit distance, the image geometry is better than in an undertable system. Due to the appropriate flipping of the X-ray radiator, an oblique positioning of the probe is possible even in the undertable operation mode, which is not the case with conventional undertable systems. By flipping away or removing the radiation protection housing with the operation unit, the X-ray system can be used, to the full extent, as an overtable device including a remote control.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray system comprising:
   an examination table having a surface adapted to receive an examination subject thereon;
   an X-ray source positionable above said surface of said examination table for emitting X-rays into an irradiation volume;
   an image acquisition unit disposed beneath said surface of said examination table on which X-rays from said X-ray source are incident for generating an X-ray image;
   a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
   a mount for said radiation housing allowing only said radiation housing to be uncoupled from said examination table; and
   an operation unit for operating at least said X-ray source disposed on said examination table and accessible from the shielded zone.

2. An X-ray system as claimed in claim 1 wherein said operation unit is disposed on said radiation protection device.

3. An X-ray system as claimed in claim 1 wherein said operation unit is integrated in said radiation protection device.

4. An X-ray system as claimed in claim 1 wherein said examination table has a longitudinal axis, and comprising a mounting arrangement for said radiation protection device and said operation unit allowing displacement of said radiation protection device and said operation unit along said longitudinal axis.

5. An X-ray system as claimed in claim 1 comprising a mounting arrangement for at least one of said radiation protection housing and said operation unit allowing said at least one of said radiation protection housing and said operation unit to be swiveled away from said surface of said examination table.

6. An X-ray system as claimed in claim 1 wherein said examination table has longitudinal sides, and wherein said radiation protection housing comprises a sidewall mounted on one of said longitudinal sides of said examination table and extending upwardly therefrom, and a spanning wall disposed at atop of said sidewall and extending across said examination table to the other of said longitudinal sides, said spanning wall having at least one region thereof penetrable by said X-rays.

7. An X-ray system as claimed in claim 6 wherein said spanning wall has two edges proceeding across said examination table, and comprising a plurality of radiation shielding blade elements hanging from said spanning wall at least one of said two edges, forming a flexible wall.

8. An X-ray system as claimed in claim 6 wherein said spanning wall has an edge at said other of said longitudinal sides of said examination table, and comprising a plurality of radiation shielding blade elements hanging from said edge of said spanning wall, forming a flexible wall.

9. An X-ray system as claimed in claim 1 comprising a mount for said operation unit allowing said operation unit to be uncoupled from said examination table.

10. An X-ray system as claimed in claim 1 wherein said examination table has a longitudinal axis and a transverse axis perpendicular to said longitudinal axis, and comprising a mount for said image acquisition unit allowing movement of said image acquisition unit in at least one of a direction along said longitudinal axis and a direction along said transverse axis.

11. An X-ray system as claimed in claim 1 wherein said image acquisition unit is mounted to said examination table.

12. An X-ray system as claimed in claim 1 comprising a table base on which said examination table is disposed, said table base being disposed completely underneath said surface and not extending beyond said surface.

13. An X-ray system comprising:
    an examination table having a surface adapted to receive an examination subject thereon;
    an X-ray source positionable above said surface of said examination table for emitting X-rays into an irradiation volume;
    an image acquisition unit disposed beneath said surface of said examination table on which X-rays from said X-ray source are incident for generating an X-ray image;
    a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
    an operation unit for operating at least said X-ray source disposed on said examination table and accessible from the shielded zone; and
    a mount for said image acquisition unit allowing swiveling of said image acquisition unit from said examination table.

14. An X-ray system comprising:
an examination table having a surface adapted to receive an examination subject thereon;
an X-ray source positionable above said surface of said examination table for emitting X-rays into an irradiation volume;
an image acquisition unit disposed beneath said surface of said examination table on which X-rays from said X-ray source are incident for generating an X-ray image;
a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
an operation unit for operating at least said X-ray source disposed on said examination table and accessible from the shielded zone; and
a mount for said image acquisition unit allowing displacement of said image acquisition unit from beneath said surface of said examination table to at least one of a position beside said examination table and a position above said examination table.

15. An X-ray system comprising:
an examination table having a surface adapted to receive an examination subject thereon;
an X-ray source positionable above said surface of said examination table for emitting X-rays into an irradiation volume;
an image acquisition unit disposed beneath said surface of said examination table on which X-rays from said X-ray source are incident for generating an X-ray image;
a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
an operation unit for operating at least said X-ray source disposed on said examination table and accessible from the shielded zone; and
a stand for said X-ray source to which said X-ray source is mounted for adjustment along each of three orthogonal axes, and around a vertical axis and around a horizontal axis.

16. An X-ray system as claimed in claim 15 wherein said stand allows displacement of said X-ray source to a position outside of an area above said examination table.

17. An X-ray system comprising:
an examination table having a surface adapted to receive an examination subject thereon;
an X-ray source positionable above said surface of said examination table for emitting X-rays into an irradiation volume;
an image acquisition unit disposed beneath said surface of said examination table on which X-rays from said X-ray source are incident for generating an X-ray image;
a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
an operation unit for operating at least said X-ray source disposed on said examination table and accessible from the shielded zone; and
a table base on which said examination table is disposed, said table base being disposed completely underneath said surface and not extending beyond said surface, said examination table having a longitudinal axis and a transverse axis perpendicular to said longitudinal axis and wherein said examination table being connected to a said table base to allow tilting of said examination table around at least one of said longitudinal axis and said transverse axis.

18. An X-ray system comprising:
an examination table having a surface adapted to receive an examination subject thereon;
an X-ray source positionable above said surface of said examination table for emitting X-rays into an irradiation volume;
an image acquisition unit disposed beneath said surface of said examination table on which X-rays from said X-ray source are incident for generating an X-ray image;
a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
an operation unit for operating at least said X-ray source disposed on said examination table and accessible from the shielded zone; and
said examination table is being mounted to said table base to allow tilting of said examination table into a vertical position.

19. An X-ray system comprising:
an examination table having a surface adapted to receive an examination subject thereon;
an X-ray source positionable above said surface of said examination table for emitting X-rays into an irradiation volume;
an image acquisition unit disposed beneath said surface of said examination table on which X-rays from said X-ray source are incident for generating an X-ray image;
a radiation protection device disposed on said examination table having a bridge-like radiation protection housing extending, at least during operation of said X-ray source, completely across said examination table between said X-ray source and said image acquisition unit and shielding a zone from said irradiation volume on at least one side of said examination table;
an operation unit for operating at least said X-ray source disposed on said examination table and accessible from the shielded zone; and
a control device connected to at least one of said image acquisition unit, said X-ray source and said examination table that automatically positions said at least one of said image acquisition unit, said X-ray source and said examination table.

20. An X-ray system as claimed in claim 19 wherein said X-rays emitted by said X-ray source include a central X-ray beam, and wherein said control device automatically positions said X-ray source, and simultaneously automatically causes said image acquisition unit to follow said X-ray source for centering said image acquisition unit with respect to said central X-ray beam.

21. An X-ray system as claimed in claim 19 wherein said X-ray emitted by said X-ray source include a central X-ray beam, and wherein said control device automatically positions said examination table, and simultaneously causes said X-ray source to automatically follow said examination table for maintaining a position and an angle of said central X-ray beam, with respect to said examination table, constant.

22. An X-ray system as claimed in claim 19 wherein said control device is selectively deactivatable for allowing manual positioning of at least one of said X-ray source, said examination table and said image acquisition unit.

* * * * *